Figure 1:
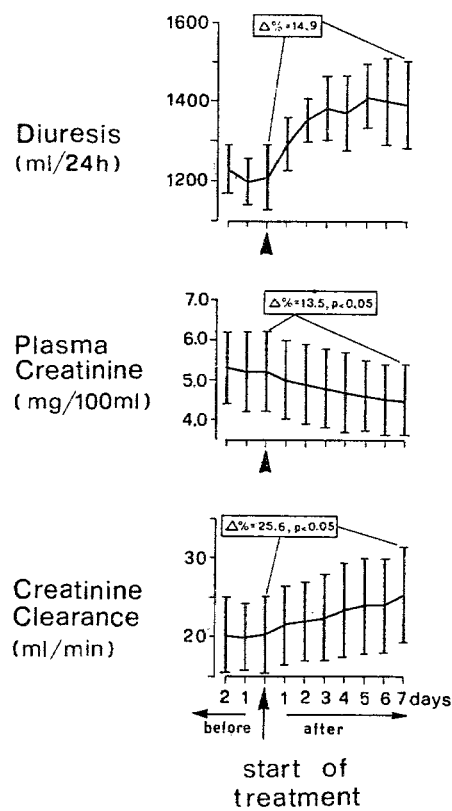

United States Patent [19]

Casagrande et al.

[11] 4,302,471
[45] Nov. 24, 1981

[54] METHOD OF TREATING CARDIAC AND RENAL FAILURES

[75] Inventors: Cesare Casagrande, Como; Giorgio Ferrari, Milan, both of Italy

[73] Assignee: Simes Societa Italian Medicinali e Sintetici S.p.A., Milan, Italy

[21] Appl. No.: 151,632

[22] Filed: May 20, 1980

Related U.S. Application Data

[60] Continuation-in-part of Ser. No. 117,211, Jan. 31, 1980, abandoned, which is a division of Ser. No. 820,007, Jul. 28, 1977, Pat. No. 4,218,470.

[30] Foreign Application Priority Data

Aug. 5, 1976 [IT] Italy ............................... 26074 A/76

[51] Int. Cl.³ .......................................... A61K 31/215
[52] U.S. Cl. .................................................... 424/311
[58] Field of Search ........................................ 424/311

[56] References Cited
PUBLICATIONS

Melloni et al., "Clinical Pilot Trail on SB7505", *Current Clinical Research*, vol. 26, No. 4, Oct. 1979, pp. 466–470.
Cicchetti et al., "Behavior of Diuresis, . . . After SB7505", *Current Clinical Research*, vol. 27, No. 5, pp. 741–747, May 1980.
Melloni et al., "Effects of SB7505 on Blood Pressure", *Current Therapeutic Research*, vol. 25, No. 3, pp. 406–414, Mar. 1979.
Arzneim, Forsch./Drug Res., Dei Cas et al., "Non-Invasive Evaluation of Ventricular Function . . . in Man", 30 (I), No. 3, pp. 498–500, (1980).
La Nouvelle Presse Medical, "Effects D'un Derive de la Dopamine Actif par voie Orale sur L'Excretion Renal", p. 453, Feb. 9, 1980.

*Primary Examiner*—Anna P. Fagelson
*Attorney, Agent, or Firm*—Cushman, Darby & Cushman

[57] ABSTRACT

The present invention relates to a method of inducing a response dopamine-like in an animal having impaired cardiovascular and renal functions, comprising administering to said animal an effective amount of a compound having the general formula:

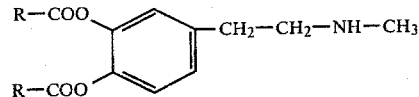

wherein R is a secondary or tertiary alkyl radical having from 3 to 7 carbon atoms, and their salts with non-toxic organic and inorganic acids.

In particular, the present invention relates to a method of treating cardiac and renal failures comprising administering to a patient suffering therefrom an effective amount of a compound having the above-identified general formula, in suitable pharmaceutical preparations.

19 Claims, 2 Drawing Figures

METHOD OF TREATING CARDIAC AND RENAL FAILURES

RELATED APPLICATIONS

This application is a continuation-in-part of our U.S. patent application Ser. No. 117,211 filed on Jan. 31, 1980 abandoned, Rule 60 divisional of U.S. Ser. No. 820,007 filed on July 28, 1977 now U.S. Pat. No. 4,218,470 the disclosure of which is hereby incorporated by reference.

The claimed therapeutic method comprises the administration of a compound having the following formula:

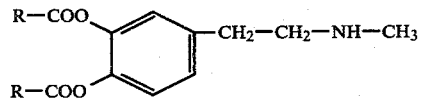

preferably as a salt with a non-toxic organic or inorganic acid. Thus, in a preferred embodiment of the invention, the administered compound is 3,4-di-o-isobutyrylepinine in the form of its hydrochloride (M.W. 343.5, m.p. 132° C. from ethyl acetate) or hydrogen succinate (M.W. 425, m.p. 118°–120° C. from ethyl acetate) or hydrogen tartrate (M.W. 457, m.p. 138°–140° C. from ethyl acetate); the dose to be administered depends on the route of administration and also on the molecular weight of the employed salts. Thus, the daily dose for oral administration ranges between 50 and 600 mg for the hydrochloride, between 60 and 700 mg, approximately, for the hydrogen succinate and between 70 and 800 mg, approximately, for the hydrogen tartrate; these daily oral doses are preferably administered in fractions, each unit dose ranging between 25 and 150 mg for the hydrochloride, 30 and 180 mg for the hydrogen succinate and 35 and 200 mg for the hydrogen tartrate.

In case of parenteral administration, the daily dose is 10 to 160 mg for the hydrochloride, in unit doses of 5 to 20 mg; the hydrogen succinate and tartrate may be administered in doses proportionally increased, according to their molecular weight, as already shown for the oral administration.

The compounds are administered in suitable pharmaceutical preparations, such as capsules or tablets with appropriate excipients, or solutions with appropriate solvents, for oral administrations as well as ampoules for parenteral administration, such ampoules containing the compounds as solutions in appropriate solvents, or in dry powder form, to be dissolved with physiologically acceptable diluent before the use.

The claimed therapeutic method is exemplified by two clinical trials in which a oral daily dose of 100 mg of 3,4-di-o-isobutyrylepinine hydrochloride, divided into two 50 mg unit doses, was administered for several days to cardiac and renal patients. The above dose had been previously shown to be effective and safe in pharmacological and toxicological experiments in laboratory animals, as well as in clinical pharmacology experiments in healthy volunteers.

The first clinical trial was carried out in 10 male patients suffering from congestive heart failure (CHF); they were classified in II (3 patients), III (4 patients) and IV (3 patients) NYHA class; hystory of heart disease ranged from 2 to 6 years.

Two patients had ischemic congestive cardiomyopathy, three myocardiosclerosis, three postnecrotic mitralic insufficiency, one idiopathic congestive cardiomyopathy, and one mitroaortic rheumatic valvular disease.

Two patients were dismissed from the study, respectively after two and three days because the severity of their clinical status required, for ethical reason, the full use of all available therapeutic methods.

The results concerning the other eight patients are therefore considered.

The treatment was preceded by two weeks of clinical observation after which 50 mg of the compound were administered orally twice a day (8:00 a.m. and 4:00 p.m.) for seven days. During these three weeks, diet and water intake were constant, $Na^+$ intake was 85 mEq/day; all other treatments were stopped with the exception of some i.v. furosemide injection, as required by emergency situations; in two patients in IV NYHA class, digoxin was continued and maintained at steady state level.

The following parameters were measured on each patients before the treatment and each day during the treatment at times 0, 4, 8 and 12 h (time 0 being the time of the first daily administration of the compound): heart rate (HR), systolic and diastolic blood pressure (SBP and DBP), and electrocardiogram, carotid pulse, and 4 phonocardiographic recordings at different frequencies (polygraphic method), diuresis, plasma concentration and urinary excretion of $Na^+$ and $K^+$. In addition clinical criteria of compensation and any possible side effects were assessed carefully each day.

Creatinine clearance, body weight and usual blood biochemical parameters were also measured before treatment and on the last day of treatment.

Two systolic time intervals, pre-ejection period (PEP) and electromechanical systole (EMS) were derived from the polygraphic recordings.

The data were processed in order to calculate mean values ± S.E.

Statistical degrees of significance were assessed by Student's "t" test for paired samples by comparing each value with the respective baseline value. In the case of diuresis, urinary excretion of electrolytes, body weight and creatinine clearance, the baseline value was the value recorded on the last day before starting the treatment.

The patients treated, including the two who were dismissed from the study are listed in Table 1; the results concerning those who had completed the treatment are listed in Tables 2–4. The results obtained may be described as follows: during the 7 days of treatment HR, SBP and DBP showed either no variations or marginal and not statistically significant variations as compared to baseline values.

PEP and EMS both decreased invariably peaking 4 hours after each administration; this decrease was on average 16.8 msec with PEP and 22.3 msec with EMS. Both PEP and EMS rose again after the 4th h and in any case were still statistically lower than baseline values at the 8th hour. This behaviour of PEP and EMS was invariably repeated throughout the treatment period.

Table 4 shows diuresis, urinary excretion of $Na^+$ and $K^+$, their ratio, creatinine clearance and body weight before and during the treatment.

In all the patients diuresis constantly improved, on average by 38.4% on the first day, 60.4% on the second, 64.1% on the thirs, 70.4% on the 4th, 89.2% on the 5th, 83.5% on the 6th and 85.4% on the 7th. Urinary excretion of $Na^+$ and $K^+$ behaved similarly, $Na^+$ increasing on average by 38.1% on the 1st day and reaching 66.2% on the 7th day and $K^+$ 37.7% on the 1st day and 47% on the 7th day, in both cases with a high degree of statistical significance. The $Na^+/K^+$ urinary ratio did not show statistically significant variations during the period of treatment.

Creatinine clearance was increased by 34.5% ($P<0.01$) and body weight decreased by 4.6% ($P<0.01$).

No variations were detected in the hematochemical parameters evaluated.

The clinical observations performed daily during the experiment on the 8 patients showed an evident improvement in cardiac compensation. No objective or subjective side effects attributable to the treatment were observed.

It may be concluded that treatment with 50 mg of 3,4-di-o-isobutyrylepinine hydrochloride twice a day by oral administration was highly effective in these patients by improving both cardiac performance and renal function.

These beneficial effects were, moreover, achieved in the absence of side effects and without changes in HR, SBP, DBP and hematochemical parameters.

TABLE 1

|  | Name | Age | Diagnosis | History of heart disease | NYHA class |
|---|---|---|---|---|---|
| Treated patients | L. W. | 58 | ischemic congestive cardiomyopathy | 3 years | 2 |
|  | C. V. | 76 | myocardiosclerosis | 3 years | 2 |
|  | C. S. | 69 | postnecrotic mitralic insufficiency | 2 years | 2 |
|  | C. E. | 73 | myocardiosclerosis | 4 years | 3 |
|  | V. R. | 65 | myocardiosclerosis | 2 years | 3 |
|  | S. F. | 58 | postnecrotic mitralic insufficiency | 4 years | 3 |
|  | B. G. | 54 | idiopatic congestive cardiomyopathy | 3 years | 4 |
|  | Q. G. | 71 | ischemic congestive cardiomyopathy | 6 years | 4 |
| patients dismissed from study | T. A. | 70 | mitroaortic rheumatic valvular disease | 5 years | 3 |
|  | C. A. | 74 | postnecrotic mitralic insufficiency | 4 years | 4 |

TABLE 2

|  |  | Baseline | Days of treatment | | | | | | |
|---|---|---|---|---|---|---|---|---|---|
|  |  |  | 1 | 2 | 3 | 4 | 5 | 6 | 7 |
| H.R. (beats/min) | 0 | 73.77 | 71.01 | 73.26 | 71.89 | 69.91 | 71.23 | 72.09 | 70.81 |
|  | * | ± 10.19 | ± 12.10 | ± 12.64 | ± 7.79 | ± 6.42 | ± 10.68 | ± 8.84 | ± 6.84 |
|  | 4 h | 74.14 | 71.28 | 72.07 | 72.63 | 71.20 | 72.74 | 71.55 | 70.02 |
|  |  | ± 10.12 | ± 9.20 | ± 8.04 | ± 10.41 | ± 6.63 | ± 7.70 | ± 7.85 | ± 5.94 |
|  | 8 h | 71.61 | 72.97 | 73.57 | 73.24 | 73.45 | 70.29 | 70.28 | 71.16 |
|  | * | ± 10.36 | ± 10.85 | ± 9.84 | ± 9.48 | ± 6.66 | ± 10.40 | ± 7.77 | ± 6.73 |
|  | 12 h | 72.95 | 73.13 | 73.75 | 72.62 | 72.18 | 74.00 | 71.96 | 72.77 |
|  |  | ± 10.97 | ± 10.42 | ± 8.70 | ± 8.60 | ± 7.70 | ± 9.22 | ± 7.14 | ± 7.13 |
| SBP (mmHg) | 0 | 130.64 | 127.50 | 130.60 | 126.25 | 125.62 | 129.37 | 124.37 | 125.00 |
|  | * | ± 21.70 | ± 18.10 | ± 29.45 | ± 17.68 | ± 17.41 | ± 18.98 | ± 20.26 | ± 22.36 |
|  | 4 h | 130.21 | 133.12 | 126.25 | 130.00 | 127.50 | 125.62 | 126.25 | 125.00 |
|  |  | ± 22.78 | ± 23.14 | ± 21.67 | ± 23.75 | ± 16.04 | ± 17.61 | ± 20.66 | ± 20.35 |
|  | 8 h | 128.96 | 128.12 | 123.12 | 131.25 | 122.50 | 128.12 | 124.37 | 128.12 |
|  | * | ± 24.14 | ± 23.90 | ± 26.04 | ± 24.31 | ± 23.15 | ± 21.54 | ± 15.45 | ± 18.89 |
|  | 12 h | 131.24 | 127.50 | 127.50 | 130.00 | 125.00 | 123.12 | 123.75 | 121.87 |
|  |  | ± 25.44 | ± 22.83 | ± 23.75 | ± 20.70 | ± 21.55 | ± 18.89 | ± 18.85 | ± 17.92 |
| DBP (mmHg) | 0 | 80.21 | 81.87 | 82.50 | 79.37 | 79.37 | 78.75 | 76.87 | 78.85 |
|  | * | ± 14.38 | ± 14.13 | ± 17.53 | ± 8.21 | ± 9.80 | ± 11.57 | ± 9.98 | ± 10.94 |
|  | 4 h | 79.36 | 84.37 | 79.37 | 81.25 | 81.25 | 80.62 | 76.87 | 79.37 |
|  |  | ± 11.56 | ± 13.74 | ± 17.00 | ± 10.94 | ± 8.35 | ± 10.50 | ± 7.99 | ± 10.50 |
|  | 8 h | 80.85 | 81.25 | 78.75 | 80.00 | 81.25 | 86.25 | 77.50 | 77.50 |
|  | * | ± 12.72 | ± 12.75 | ± 17.88 | ± 13.02 | ± 10.35 | ± 15.98 | ± 7.56 | ± 9.26 |
|  | 12 h | 82.29 | 81.87 | 83.75 | 80.00 | 80.62 | 79.37 | 80.62 | 77.50 |
|  |  | 12.66 | 13.87 | 15.53 | 11.02 | 12.94 | 10.50 | 9.04 | 7.56 |

TABLE 3

|  |  | Baseline | Days of treatment | | | | | | |
|---|---|---|---|---|---|---|---|---|---|
|  |  |  | 1 | 2 | 3 | 4 | 5 | 6 | 7 |
| PEP (msec) | 0 | 137.50 | 137.50 | 137.5 | 135.0 | ** 135.0 | 137.5 | 136.87 | 136.87 |
|  | * | ± 11.2 *** | ± 10.7 *** | ± 10.7 ** | ± 10.7 *** | ± 11.3 ** | ± 12.5 *** | ± 12.2 *** | ± 10.3 *** |
|  | 4 h | 137.3 | 119.37 | 121.87 | 120.0 | 122.5 | 122.5 | 117.50 | 119.37 |
|  |  | ± 11.0 | ± 12.1 ** | ± 14.4 ** | ± 14.9 * | ± 14.6 ** | ± 10.0 * | ± 13.9 ** | ± 12.9 ** |
|  | 8 h | 136.65 | 128.75 | 130.0 | 131.25 | 130.62 | 132.50 | 131.25 | 130.62 |
|  | * | ± 10.6 *** | ± 11.9 *** | ± 12.2 ** | ± 10.9 ** | ± 12.7 *** | ± 12.2 ** | ± 10.9 *** | ± 11.5 *** |
|  | 12 h | 138.33 | 118.75 | 118.75 | 120.62 | 120.62 | 123.75 | 118.75 | 120.62 |
|  |  | ± 11.5 | ± 9.5 | ± 13.5 | ± 14.5 | ± 14.5 | ± 14.6 | ± 12.2 | ± 11.2 |
| EMS | 0 | 382.5 | 383.2 | 381.0 | 380.0 | 376.1 | 382.4 | 378.6 | 381.6 |

TABLE 3-continued

|  |  | Baseline | Days of treatment | | | | | | |
|---|---|---|---|---|---|---|---|---|---|
|  |  |  | 1 | 2 | 3 | 4 | 5 | 6 | 7 |
| (msec) |  | * ± 13.0 | ± 12.0 *** | ± 9.4 *** | ± 16.5 *** | ± 15.1 ** | ± 12.6 ** | ± 11.1 *** | ± 15.8 *** |
|  | 4 h | 318.5 ± 11.6 | 361.9 ± 14.2 * | 359.3 ± 12.2 | 360.2 ± 15.7 | 360.6 ± 18.0 | 365.3 ± 11.4 | 354.7 ± 10.9 ** | 352.6 ± 15.2 * |
|  | 8 h | 380.9 ° ± 12.9 | 371.1 ± 10.6 *** | 374.7 ± 19.4 ** | 374.7 ± 18.3 ** | 372.2 ± 18.1 * | 372.3 ± 16.3 ** | 366.2 ± 14.1 ** | 366.8 ± 17.2 ** |
|  | 12 h | 386.9 ± 16.9 | 357.1 ± 15.3 | 360.4 ± 16.1 | 362.6 ± 19.7 | 362.1 ± 20.1 | 364.1 ± 20.1 | 352.9 ± 23.8 | 354.7 ± 19.1 |

TABLE 4

|  | Baseline | Days of treatment | | | | | | |
|---|---|---|---|---|---|---|---|---|
|  |  | 1° | 2° | 3° | 4° | 5° | 6° | 7° |
|  |  | ** | *** | ** | *** | *** | *** | *** |
| Diuresis (ml/day) | 997.8 ± 286.6 | 1381.3 ± 302.2 * | 1600.0 ± 293.4 * | 1637.5 ± 369.8 ** | 1700.0 ± 364.8 ** | 1887.5 ± 421.1 ** | 1831.3 ± 377.7 ** | 1850.0 ± 185.4 ** |
| urinary Na+ (mEq/day) | 83.2 ± 36.3 | 114.9 ± 40.4 * | 130.0 ± 45.8 ** | 138.2 ± 44.1 ** | + ± 39.9 ** | 133.9 ± 38.6 ** | 136.0 ± 35.4 ** | 138.4 ± 31.8 ** |
| urinary K+ (mEq/day) | 30.9 ± 6.6 | 41.0 ± 11.8 | 41.6 ± 7.4 | 45.0 ± 9.1 | 43.4 ± 10.5 | 41.1 ± 9.1 | 43.4 ± 8.6 | 45.4 ± 8.4 |
| Na+/K+ | 2.7 | 2.8 | 3.1 | 3.1 | 3.2 | 3.2 | 3.1 | 3.0 * |
| creatinine clearance (ml/min) | 56.8 ± 28.8 |  |  |  |  |  |  | 79.1* ± 28.1 * |
| body weight (kg) | 68.7 ± 10.7 |  |  |  |  |  |  | 65.5* ± 10.8 |

The second clinical trial was performed on a group of patients showing various degrees of impairment in renal function (Table 5).

Patients were treated with the compound (50 mg) per os twice a day (8 a.m. and 6 p.m.) for seven days; a nurse was present when the drug was taken. Treatment with other drugs was stopped 5-7 days before starting the treatment.

Three days before and every day during treatment the following parameters were assessed: systolic and diastolic blood pressure SBP, DBP), heart rate (HR), body weight (BW), 24 h diuresis (D) plasma creatinine (C), creatinine clearance (Ccr), urinary Na+ and K+ excretion ($Na_u^+$, $K_u^+$). Plasma Na+ and K+ ($Na_p^+$, $K_p^+$) were measured before treatment and on the third and seventh days. In addition ECG, blood glucose, BUN, SGOT, SGPT, gamma GT, alkaline phosphatase, bilirubin and plasma proteins were recorded before and after treatment in order to assess drug tolerance. Daily urinary excretion of two enzymes (lysozime and gamma GT) was also measured, as a check on possible kidney damage deriving from the drug.

Careful clinical evaluation was kept up throughout treatment. The patients had a protein intake reduced according to the degree of residual renal function. Care was taken in all cases to make no changes in diet compared with the days preceding the treatment. Sodium and fluid intake were carefully dosed in each case. All the data obtained were computerized and statistical evaluation was performed by Student's t-test for paired samples comparing the data recorded the day before starting the treatment and that recorded on the last day of treatment.

The behaviour of diuresis, plasma creatinine and creatinine clearance is illustrated in FIG. 1.

The treatment led to progressive increase in diuresis of 14.9% (P<0.10).

Figure 2:
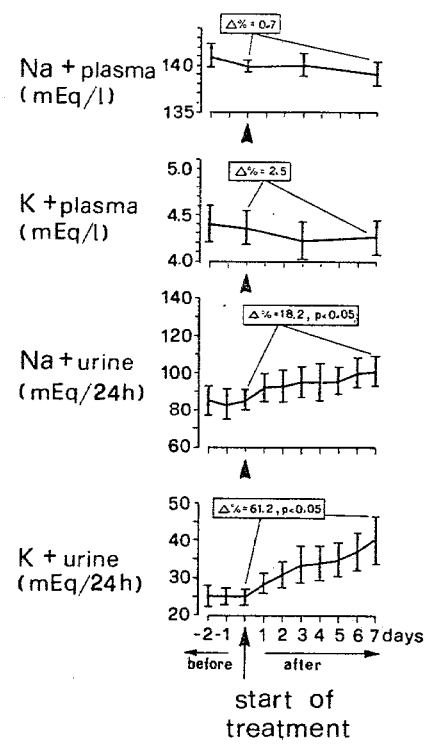

Plasma concentration of creatinine decreased by 13.5%, while creatinine clearance significantly increased by 25.6%. The urinary excretion of sodium and potassium increased by 18.2% and 61.2% respectively (FIG. 2).

Body weight, heart rate, systolic blood pressure and diastolic blood pressure did not change significantly (Table 6).

The clinical tolerance of the drug throughout treatment was good. No side-effects or changes in the hematological parameters were observed. No variation was detected in the daily urinary excretion of lysozime and gamma GT.

The results confirm the activity of the test compound in patients with impaired renal function. The treatment induced an increase of diuresis and an increase in urinary excretion of sodium and potassium, although to a lesser degree than in volunteers with normal renal functions. As far as plasma creatinine and creatinine clearance are concerned, the patients showed a decrease in the former and an increase in the latter; these results appear of particular relevance, since at present there is a lack of drugs who can induce such favourable effects in kidney failure.

The absence of variations in the daily urinary excretion of lysozime and gamma GT rules out any direct nephrotoxic action of the treatment. Heart rate and arterial pressure were also unaffected.

TABLE 5

| | | | Characteristics of the patients with impaired renal functions. | | |
|---|---|---|---|---|---|
| SUBJECTS | SEX | AGE | DIAGNOSIS | C (mg/100 ml) | Ccr (ml/min) |
| G.L. | M | 39 | Chronic Interstitial Nephritis | 8.9 | 9 |
| B.V. | M | 60 | Chronic Pyelonephritis | 2.4 | 38 |
| D.L. | M | 24 | Hereditary Nephropathy | 2.6 | 35 |
| G.A.M. | F | 41 | Hereditary Nephropathy | 6.0 | 13 |
| F.O. | M | 65 | Chronic Interestitial Nephritis | 6.0 | 12 |
| B.L. | M | 52 | Chronic Glomerulonephritis | 4.3 | 18 |

C = plasma creatinine
Ccr = creatinine clearance

TABLE 6

| | BEFORE | AFTER |
|---|---|---|
| HR (beats/min) | 72.4 ± 1.3 | 73.7 ± 1.2 |
| SBP (mmHg) | 135.2 ± 4.0 | 137.6 ± 5.0 |
| DBP (mmHg) | 88.5 ± 3.2 | 89.3 ± 3.4 |
| BW (Kg) | 71.7 ± 6.0 | 71.4 ± 5.7 |

Beneficial effect were also observed in a further clinical experiment aimed at evaluating hemodynamic modifications in congestive cardiomyopathy patients carrying a cardiac catheter. Thus, for example, a patient (V.L., male, aged 67), subjected to surgery for ventricular aneurismectomy and to right heart catheterization was administered an oral unit dose of 150 mg of 3,4-di-O-isobutyrylepinine hydrochloride. Hemodynamic parameters, assessed by thermodilution technique, are reported in table 7; a marked increase in cardiac output and a decrease in pulmonary pressure was observed. Diuresis was also remarkably increased, totalling 3400 ml in 24 hours.

TABLE 7

| | Time from administration (hours) | | | | |
|---|---|---|---|---|---|
| | 0 | 2 | 4 | 6 | 10 |
| Cardiac output (1/min) | 2.06 | 3.86 | 2.93 | 2.49 | 2.74 |
| Mean pulmonary pressure (mmHg) | 41 | 35 | 23 | 31 | 35 |
| Right atrial pressure (mmHg) | 7 | 3 | 6 | 7 | 2 |
| Heart rate (beats/min) | 100 | 100 | 100 | 100 | 100 |

We claim:

1. A method for inducing a response dopamine-like in an animal having impaired cardiovascular or renal functions, comprising administering to said animal an effective amount therefor of a compound having the general formula:

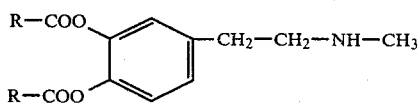

wherein R is a secondary or tertiary alkyl radical having from 3 to 7 carbon atoms, and their salts with non-toxic organic and inorganic acids.

2. The method of claim 1, wherein said compound is 3,4-di-0-isobutyrylepinine, having the formula (1) for R=isopropyl.

3. The method of claim 1, wherein said compound is 3,4-di-O-pivaloylepinine having the formula (1) for R=tert.butyl.

4. A method of treating congestive heart failure or impared renal function comprising administering to a patient suffering therefrom an effective amount of a compound having the following general formula:

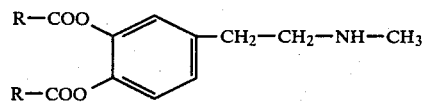

wherein R is a secondary or tertiary alkyl radical having from 3 to 7 carbon atoms, and their salts with non-toxic organic and inorganic acids, in suitable pharmaceutical preparations.

5. A method according to claim 4, wherein said compound is orally administered.

6. A method according to claim 4, wherein said compound is parenterally administered.

7. A method according to claim 4, wherein said compound is 3,4-di-O-isobutyrylepinine.

8. A method according to claim 7, wherein said compound is the hydrochloride salt thereof.

9. A method according to claim 8, wherein said compound is orally administered according to an effective amount comprised in the range from 50 to 600 mg/die.

10. A method according to claim 9, wherein said effective amount is administered in unit doses ranging from 25 to 150 mg, each.

11. A method according to claim 8, wherein said compound is parenterally administered in an effective amount comprised in the range from 10 to 160 mg/die.

12. A method according to claim 11, wherein said effective amount is administered in unit doses ranging from 5 to 20 mg each.

13. A method according to claim 7, wherein said compound is the hydrogen succinate salt thereof.

14. A method according to claim 13, wherein said compound is orally administered in an effective amount comprised in the range from 60 to 700 mg/die.

15. A method according to claim 14, wherein said effective amount is administered in unit doses ranging from 30 to 180 mg each.

16. A method according to claim 13, wherein said compound is parenterally administered.

17. A method according to claim 7, wherein said compound is the hydrogen tartrate salt thereof.

18. A method according to claim 17, wherein said compound is orally administered in an effective amount comprised in the range from 70 to 800 mg/die.

19. A method according to claim 18, wherein said effective amount is administered in unit doses ranging from 35 to 200 mg each.

* * * * *